United States Patent
Mastri et al.

(10) Patent No.: US 9,545,264 B2
(45) Date of Patent: Jan. 17, 2017

(54) TROCARS AND OBTURATORS

(71) Applicant: SurgiQuest, Inc., Milford, CT (US)

(72) Inventors: Dominick Mastri, Bridgeport, CT (US); Michael Augelli, Prospect, CT (US); Michael Kane, Clinton, CT (US)

(73) Assignee: Surgiquest, Inc., Milford, CT (US)

( * ) Notice: Subject to any disclaimer, the term of this patent is extended or adjusted under 35 U.S.C. 154(b) by 57 days.

(21) Appl. No.: 14/298,149

(22) Filed: Jun. 6, 2014

(65) Prior Publication Data
US 2015/0351794 A1  Dec. 10, 2015

(51) Int. Cl.
*A61B 17/34* (2006.01)
*A61B 17/00* (2006.01)

(52) U.S. Cl.
CPC ........... *A61B 17/3423* (2013.01); *A61B 17/34* (2013.01); *A61B 17/3417* (2013.01); *A61B 17/3474* (2013.01); *A61B 2017/00429* (2013.01); *A61B 2017/00473* (2013.01); *A61B 2017/00477* (2013.01); *A61B 2017/00862* (2013.01); *A61B 2017/00907* (2013.01); *A61B 2017/346* (2013.01); *A61B 2017/3454* (2013.01); *A61B 2017/3456* (2013.01); *A61B 2017/3466* (2013.01)

(58) Field of Classification Search
CPC ................. A61M 2039/025–2039/0297; A61B 2017/349; A61B 17/34–17/3498
USPC ............... 215/284, 280, 277, 273, 216, 215, 225,215/224; 220/326, 324, 315, 284; 604/165.01–165.04
See application file for complete search history.

(56) References Cited

U.S. PATENT DOCUMENTS

| | | | | |
|---|---|---|---|---|
| 3,802,607 A | * | 4/1974 | Mead | B65D 83/40 215/201 |
| 3,820,683 A | * | 6/1974 | Jasinski | B65D 83/40 215/216 |
| 3,854,622 A | * | 12/1974 | McKirnan | B65D 83/40 215/206 |
| 3,907,103 A | * | 9/1975 | Shaw | B65D 43/162 206/1.5 |
| 3,995,765 A | * | 12/1976 | Burke | B65D 83/40 215/204 |
| 4,172,533 A | * | 10/1979 | Montgomery | B65D 50/046 215/216 |
| 4,588,097 A | * | 5/1986 | Hauser | B65D 50/045 215/216 |

(Continued)

*Primary Examiner* — Jacqueline Johanas
(74) *Attorney, Agent, or Firm* — Locke Lord LLP; Scott D. Wofsy

(57) ABSTRACT

A trocar assembly includes a trocar including an elongated tubular member extending between a distal end configured to be inserted into a surgical site and a proximal end including a housing configured for introduction of surgical instruments into the tubular member. The housing includes a pair of opposed latch receptacles. An obturator is assembled into the tubular member of the trocar. The obturator includes an elongated obturator body extending from a trocar cover to an opposed obturator tip. The trocar cover includes a rim for engaging the housing of the trocar. The trocar cover includes a pair of opposed latches extending radially inward from the rim, wherein the latches are releasably latched to the latch receptacles of the trocar. The trocar cover includes a compliant mechanism operatively connected to release the latches from the latch receptacles.

18 Claims, 7 Drawing Sheets

(56) References Cited

U.S. PATENT DOCUMENTS

| | | | |
|---|---|---|---|
| 4,790,442 A * | 12/1988 | Gach | B65D 47/0885 215/216 |
| 5,256,149 A | 10/1993 | Banik et al. | |
| 5,356,421 A | 10/1994 | Castro | |
| 5,385,552 A | 1/1995 | Haber et al. | |
| 5,401,248 A | 3/1995 | Bencini | |
| 5,738,628 A * | 4/1998 | Sierocuk | A61B 17/3421 600/104 |
| 5,772,678 A | 6/1998 | Thomason et al. | |
| 5,817,061 A * | 10/1998 | Goodwin | A61B 17/3417 600/121 |
| 5,904,699 A * | 5/1999 | Schwemberger | A61B 17/3496 604/164.08 |
| 5,988,412 A * | 11/1999 | Minnette | B65D 50/046 215/206 |
| 6,017,356 A | 1/2000 | Frederick et al. | |
| 6,106,539 A | 8/2000 | Fortier | |
| 6,228,059 B1 | 5/2001 | Astarita | |
| 6,544,277 B1 | 4/2003 | O'Heeron et al. | |
| 6,783,516 B2 | 8/2004 | O'Heeron et al. | |
| 6,830,578 B2 | 12/2004 | O'Heeron et al. | |
| 6,835,201 B2 | 12/2004 | O'Heeron et al. | |
| 7,530,470 B1 * | 5/2009 | Houser | B65D 50/046 220/281 |
| 7,597,701 B2 | 10/2009 | Hueil et al. | |
| 7,637,896 B2 | 12/2009 | Voegele et al. | |
| 7,762,419 B2 * | 7/2010 | Suga | F01M 11/0408 215/216 |
| 7,846,134 B1 | 12/2010 | Nadolski et al. | |
| 8,051,999 B2 * | 11/2011 | Carmody | B65D 41/0471 215/216 |
| 8,221,364 B2 | 7/2012 | Voegele et al. | |
| 8,246,586 B2 * | 8/2012 | Schweitzer | A61B 17/3498 604/164.01 |
| 8,287,497 B2 | 10/2012 | Heinrich et al. | |
| 8,317,815 B2 | 11/2012 | Mastri et al. | |
| 8,540,745 B2 * | 9/2013 | Criscuolo | A61B 17/0218 606/190 |
| 9,078,698 B2 * | 7/2015 | Smith | A61B 17/3417 |
| 9,113,953 B2 * | 8/2015 | Smith | A61B 17/3417 |
| 2001/0029387 A1 * | 10/2001 | Wolf | A61B 17/3496 606/184 |
| 2002/0026207 A1 * | 2/2002 | Stellon | A61B 17/3496 606/185 |
| 2002/0183775 A1 * | 12/2002 | Tsonton | A61B 17/3417 606/185 |
| 2003/0004529 A1 * | 1/2003 | Tsonton | A61B 17/3462 606/185 |
| 2005/0004592 A1 * | 1/2005 | Criscuolo | A61B 17/0218 606/190 |
| 2005/0070850 A1 * | 3/2005 | Albrecht | A61B 17/34 604/167.03 |
| 2005/0070851 A1 * | 3/2005 | Thompson | A61B 17/3462 604/167.03 |
| 2005/0070943 A1 * | 3/2005 | Hueil | A61B 17/34 606/167 |
| 2005/0070946 A1 * | 3/2005 | Franer | A61B 17/3498 606/185 |
| 2005/0070947 A1 * | 3/2005 | Franer | A61B 17/3462 606/185 |
| 2005/0077688 A1 * | 4/2005 | Voegele | A61B 17/3462 277/628 |
| 2005/0077689 A1 * | 4/2005 | Hueil | A61B 17/3421 277/628 |
| 2006/0229655 A1 * | 10/2006 | Voegele | A61B 17/3417 606/190 |
| 2006/0237481 A1 * | 10/2006 | Ho | B65D 50/045 222/153.13 |
| 2006/0264992 A1 * | 11/2006 | Franer | A61B 17/3462 606/167 |
| 2007/0088241 A1 * | 4/2007 | Brustad | A61B 17/02 602/60 |
| 2007/0088277 A1 * | 4/2007 | McGinley | A61B 17/3462 604/167.01 |
| 2008/0009797 A1 * | 1/2008 | Stellon | A61B 17/3496 604/164.08 |
| 2008/0097506 A1 * | 4/2008 | Criscuolo | A61B 17/0218 606/190 |
| 2008/0161720 A1 | 7/2008 | Nicoson et al. | |
| 2008/0249475 A1 * | 10/2008 | Albrecht | A61B 17/3498 604/167.06 |
| 2008/0294111 A1 * | 11/2008 | Tal | A61M 25/0097 604/165.01 |
| 2009/0281498 A1 * | 11/2009 | Acosta | A61F 5/0003 604/164.01 |
| 2009/0306697 A1 * | 12/2009 | Fischvogt | A61B 17/3421 606/185 |
| 2010/0160938 A9 * | 6/2010 | Franer | A61B 17/3462 606/167 |
| 2010/0320168 A1 * | 12/2010 | Bull | B65D 50/046 215/219 |
| 2011/0040149 A1 * | 2/2011 | Smith | A61B 1/3132 600/114 |
| 2011/0087159 A1 | 4/2011 | Parihar et al. | |
| 2011/0218565 A1 * | 9/2011 | Criscuolo | A61B 17/0218 606/192 |
| 2011/0237901 A1 * | 9/2011 | Duke | A61B 17/3462 600/208 |
| 2011/0251559 A1 * | 10/2011 | Tal | A61M 25/0097 604/165.01 |
| 2012/0010569 A1 | 1/2012 | Parihar | |
| 2012/0228357 A1 * | 9/2012 | Milliman | A61B 17/068 227/175.2 |
| 2012/0248129 A1 * | 10/2012 | Yoshida | B65D 41/16 220/780 |
| 2013/0072955 A1 * | 3/2013 | Milliman | A61B 17/115 606/185 |
| 2013/0110151 A1 * | 5/2013 | Criscuolo | A61B 17/0218 606/190 |
| 2013/0218188 A1 | 8/2013 | McFarlane | |
| 2013/0226094 A1 * | 8/2013 | Ahmed | A61B 17/3468 604/164.04 |
| 2013/0237902 A1 * | 9/2013 | McGinley | A61B 17/3462 604/26 |
| 2013/0256163 A1 * | 10/2013 | Cottle | A24F 15/00 206/265 |
| 2013/0345512 A1 | 12/2013 | Smith et al. | |
| 2015/0038996 A1 * | 2/2015 | Malkowski | A61M 5/329 606/148 |
| 2015/0038997 A1 * | 2/2015 | Malkowski | A61M 5/329 606/148 |
| 2015/0065804 A1 * | 3/2015 | Kleyman | A61B 17/3417 600/204 |
| 2015/0173792 A1 * | 6/2015 | McGinley | A61B 17/3462 600/204 |

\* cited by examiner

TROCARS AND OBTURATORS

BACKGROUND OF THE INVENTION

1. Field of the Invention

The present disclosure relates to medical devices, and more particularly to trocars and obturators for use in laparoscopic and percutaneous surgical procedures, for example.

2. Description of Related Art

Laparoscopic, or "minimally invasive" surgical techniques have become common. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable, in order to maintain the pneumoperitoneum. During typical laparoscopic procedures, a surgeon makes three to four small incisions, usually no larger than about twelve millimeters each, which are typically made with the trocar devices themselves, typically using a separate inserter or obturator placed therein. Following insertion, the inserter is removed, and the trocar allows access for instruments to be inserted into the abdominal cavity.

The trocar can provide a means to maintain the pressure within the cavity, so that the surgeon has an open interior space in which to work, by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments.

Such conventional methods and systems have generally been considered satisfactory for their intended purpose. However, there is still a need in the art for improved trocars, obturators, and the like. The present disclosure provides a solution for this need.

SUMMARY OF THE INVENTION

A trocar assembly includes a trocar including an elongated tubular member extending between a distal end configured to be inserted into a surgical site and a proximal end including a housing configured for introduction of surgical instruments into the tubular member. The housing includes a pair of opposed latch receptacles. An obturator is assembled into the tubular member of the trocar. The obturator includes an elongated obturator body extending from a trocar cover to an opposed obturator tip. The trocar cover includes a rim for engaging the housing of the trocar. The trocar cover includes a pair of opposed latches extending radially inward from the rim, wherein the latches are releasably latched to the latch receptacles of the trocar. The trocar cover includes a compliant mechanism operatively connected to release the latches from the latch receptacles.

The compliant mechanism can include a pair of opposed pinch regions circumferentially offset from the latches. The compliant mechanism can be configured to move the latches from latched positions to release positions radially outward from the latched positions upon pinching the pinch regions toward one another. Each of the pinch regions can include a textured surface to facilitate actuation of the compliant mechanism. The trocar cover can include an anti-rotation key engaged to an anti-rotation key receptacle defined in the housing of the trocar to resist relative rotation of the trocar and obturator.

The obturator tip can include a latch receptacle and an anti-rotation key, wherein the obturator body includes a latch engaged in the latch receptacle of the obturator tip, and wherein the obturator body includes an anti-rotation key receptacle engaged to the anti-rotation key of the obturator tip.

The obturator tip can include a second anti-rotation key opposed to the first anti-rotation key and the obturator body can include a second anti-rotation key receptacle opposed to the first anti-rotation key receptacle. The first and second anti-rotation keys can be engaged to the first and second anti-rotation key receptacles, respectively.

The obturator tip can include a second latch receptacle opposed to the first latch receptacle of the obturator tip. The obturator body can include a second latch opposed to the first latch of the obturator body. The first and second latches of the obturator body can be engaged to the first and second latch receptacles of the obturator tip, respectively.

The obturator tip can include an engagement member extending into and engaged with an interior bore of the obturator body. The engagement member can include a hard stop surface blocking a radially outward portion of the interior bore for providing a hard stop to endoscopes moving within the interior bore. The engagement member can be sealingly engaged to the interior bore of the obturator body to prevent leakage between the obturator body and the obturator tip. The engagement member can include a full annular sealing surface sealed to the interior bore of the obturator body, e.g. proud of the latches and anti-rotation keys.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
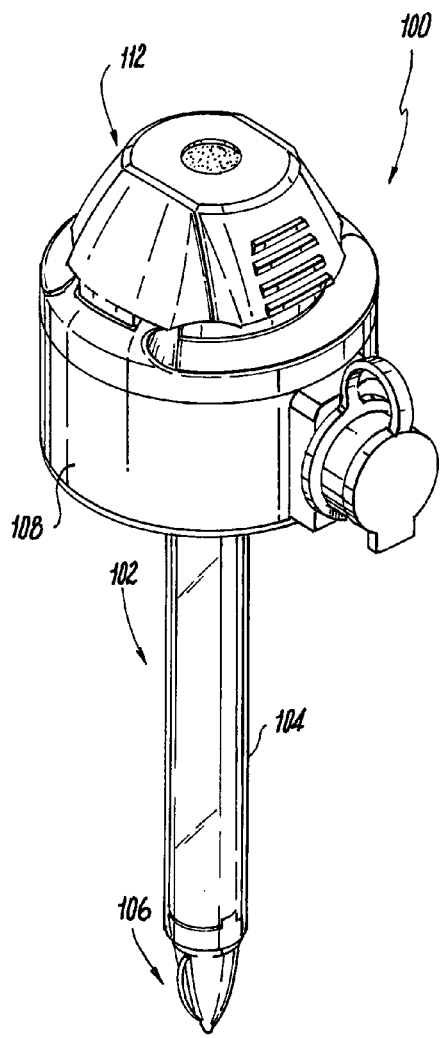
FIG. 1 is a perspective view of an exemplary embodiment of a trocar assembly constructed in accordance with the present disclosure, showing the obturator assembled into the trocar.

Reference will now be made to the drawings wherein like reference numerals identify similar structural features or aspects of the subject disclosure. For purposes of explanation and illustration, and not limitation, a partial view of an exemplary embodiment of a trocar assembly in accordance with the disclosure is shown in FIG. 1 and is designated generally by reference character 100. Other embodiments of trocar assemblies in accordance with the disclosure, or aspects thereof, are provided in FIGS. 2-9, as will be described. The systems and methods described herein can be used for laparoscopic and percutaneous procedures, for example.

Figure 4:
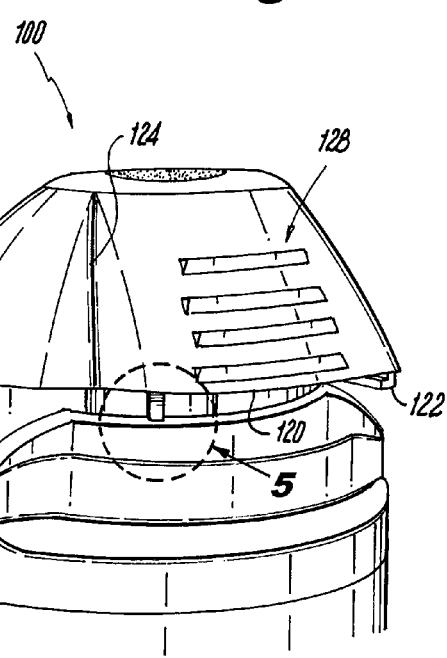
FIG. 4 is a perspective view of a portion of the trocar assembly of FIG. 1, showing the obturator unlatched from the trocar.

Trocar assembly 100 includes a trocar 102 including an elongated tubular member 104 extending between a distal end 106 configured to be inserted into a surgical site and a proximal end including a housing 108 configured for introduction of surgical instruments into the tubular member 104. Housing 108 includes a pair of opposed latch receptacles 110, one of which is shown in FIG. 4. An obturator 112 is assembled into the tubular member 104 of trocar 102.

Figure 2:
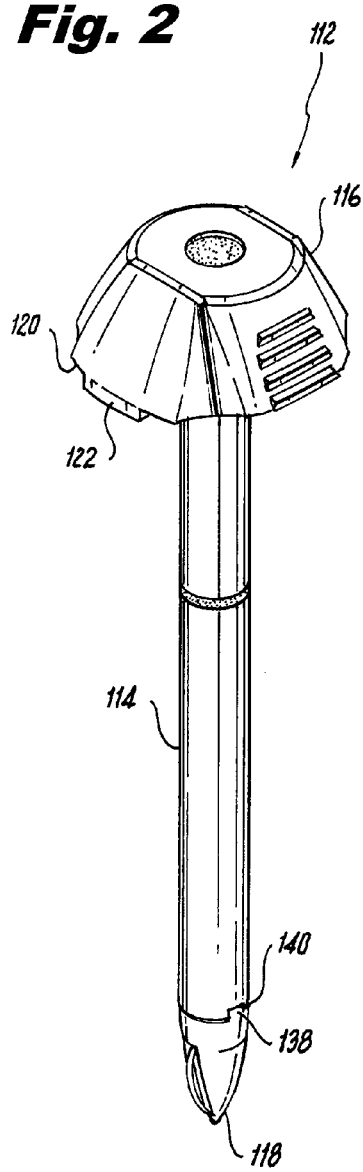
FIG. 2 is a perspective view of the obturator of FIG. 1, showing the obturator removed from the trocar.

Referring now to FIG. 2, obturator 112 includes an elongated obturator body 114 extending from a trocar cover 116 to an opposed obturator tip 118. Trocar cover 116 includes a rim 120 for engaging the housing 108 of trocar 102. Trocar cover 116 includes a pair of opposed latches 122 extending radially inward from rim 120, wherein the latches 122 are releasably latched to the latch receptacles 110 of the trocar. Trocar cover 116 includes a compliant mechanism 124 operatively connected to release the latches 122 from the latch receptacles 110.

Figure 3:
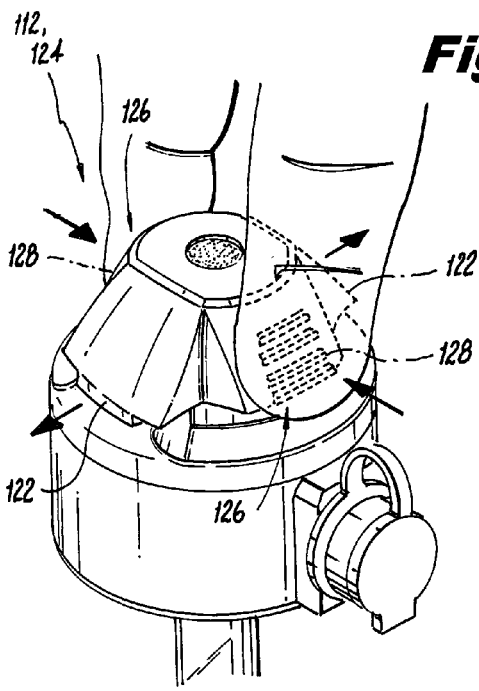
FIG. 3 is a perspective view of the trocar cover of the obturator of FIG. 2, schematically indicating the latch release action of the compliant mechanism when the pinch points are pinched together.

With reference now to FIG. 3, the compliant mechanism 124 includes a pair of opposed pinch regions 126 circumferentially offset from the latches 122. The compliant mechanism 124 is configured to move the latches 122 from their latched positions to release positions radially outward from the latched positions upon pinching the pinch regions toward one another. The release position is indicated schematically with the outward pointing arrows in FIG. 3. The pinching motion, e.g., manual pinching by a surgeon, is indicated schematically by the fingers and inward pointing arrows in FIG. 3, and the resultant outward motion of latches 122 is indicated schematically in FIG. 3 with the outward pointing arrows. Each of the pinch regions 126 includes a textured surface 128 to facilitate actuation of the compliant mechanism 124.

Figure 5:
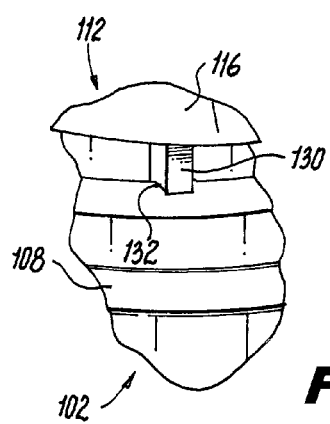
FIG. 5 is a perspective view of a portion of the trocar assembly of FIG. 4, showing the anti-rotation key and corresponding receptacle of the housing of the trocar.
Figure 6:
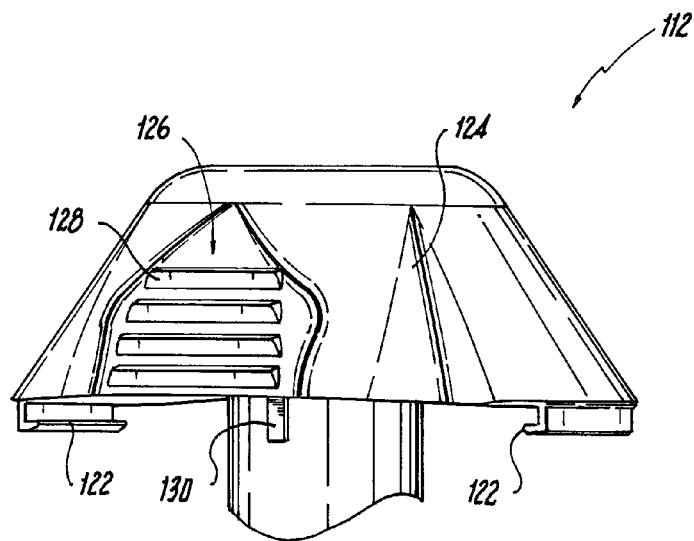
FIG. 6 is a perspective view of a portion of the obturator of FIG. 2, showing the opposed latches extending radially inward from the rim of the trocar cover.
Figure 7:
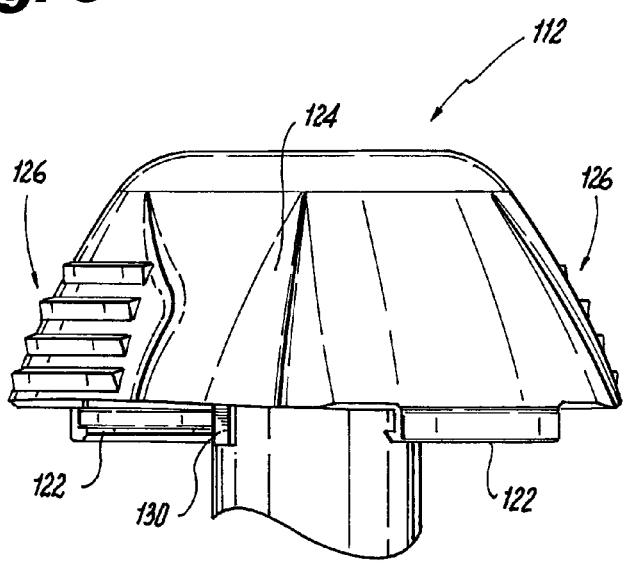
FIG. 7 is a perspective view of a portion of the obturator of FIG. 2, showing the trocar cover from a view point generally opposite of that of FIG. 6.

Referring now to FIGS. 4 and 5, trocar assembly 100 is shown prior to latching or after unlatching obturator 112 from trocar 102. FIG. 4 shows trocar assembly 100 with latches 122 of obturator 112 released from housing 108. Trocar cover 116 includes an anti-rotation key 130 engaged to an anti-rotation key receptacle 132 defined in housing 108 of trocar 102 to resist relative rotation of the trocar 102 and obturator 112, as shown in FIG. 5. Two opposed anti-rotation keys 130 are included in obturator 112, as shown in FIGS. 6-7. FIGS. 6-7 also show both of the latches 122 extending radially inward from rim 120.

Figure 8:
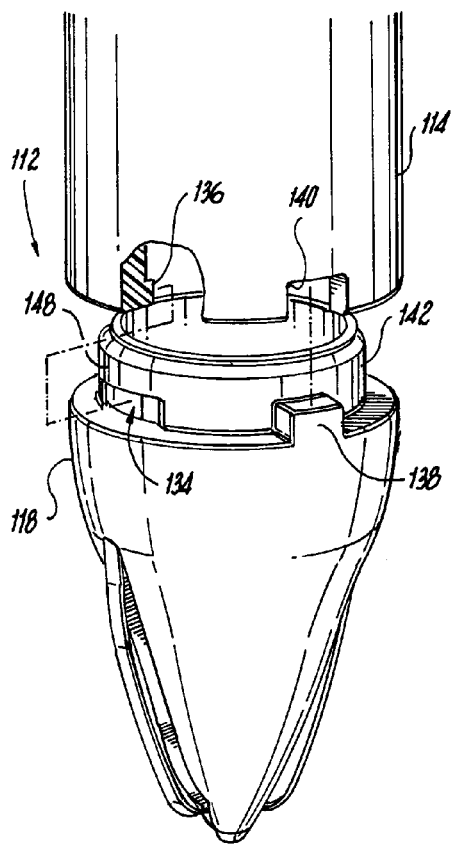
FIG. 8 is a partially cut away exploded perspective view of a portion of the obturator of FIG. 2, showing the obturator tip exploded away from the obturator body.
Figure 9:
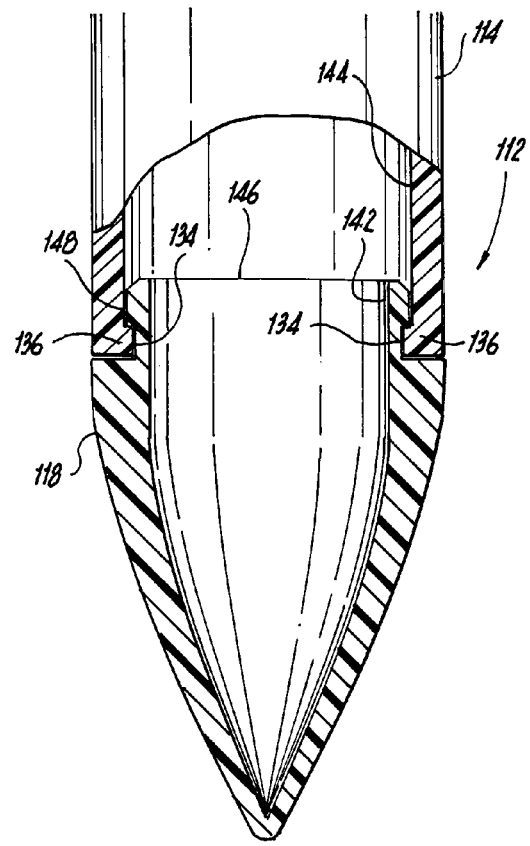
FIG. 9 is a cross-sectional side elevation view of the obturator of FIG. 8, showing the obturator tip assembled onto the obturator body.

With reference now to FIGS. 8-9, obturator tip 118 is described in greater detail. Obturator tip 118 includes a pair of opposed latch receptacles 134. Obturator body 114 includes a pair of opposed latches 136, each engaged in the respective latch receptacle 134 of the obturator tip, as shown in FIG. 9.

Obturator tip 118 also includes a pair of diametrically opposed anti-rotation keys 138 circumferentially offset from the latch receptacles 134 by 90°. Obturator body 114 includes a pair of diametrically opposed anti-rotation key receptacles 140 each engaged to a respective one of the anti-rotation keys 138. While only one anti-rotation key and receptacle are shown in FIG. 8, the other side is shown in FIG. 2.

Obturator tip 118 includes an annular engagement member 142 extending into and engaged with interior bore 144 of obturator body 114. Engagement member 142 includes a hard stop surface 146 blocking a radially outward portion of interior bore 144 for providing a hard stop to endoscopes moving within interior bore 144. Engagement member 142 is sealingly engaged to the surface of interior bore 144 to prevent leakage between obturator body 114 and obturator tip 118. Engagement member 142 includes a full annular sealing surface 148 sealed to interior bore 144, e.g. proud of the latches 136 and anti-rotation keys 138 as oriented in FIG. 8.

Figure 10:
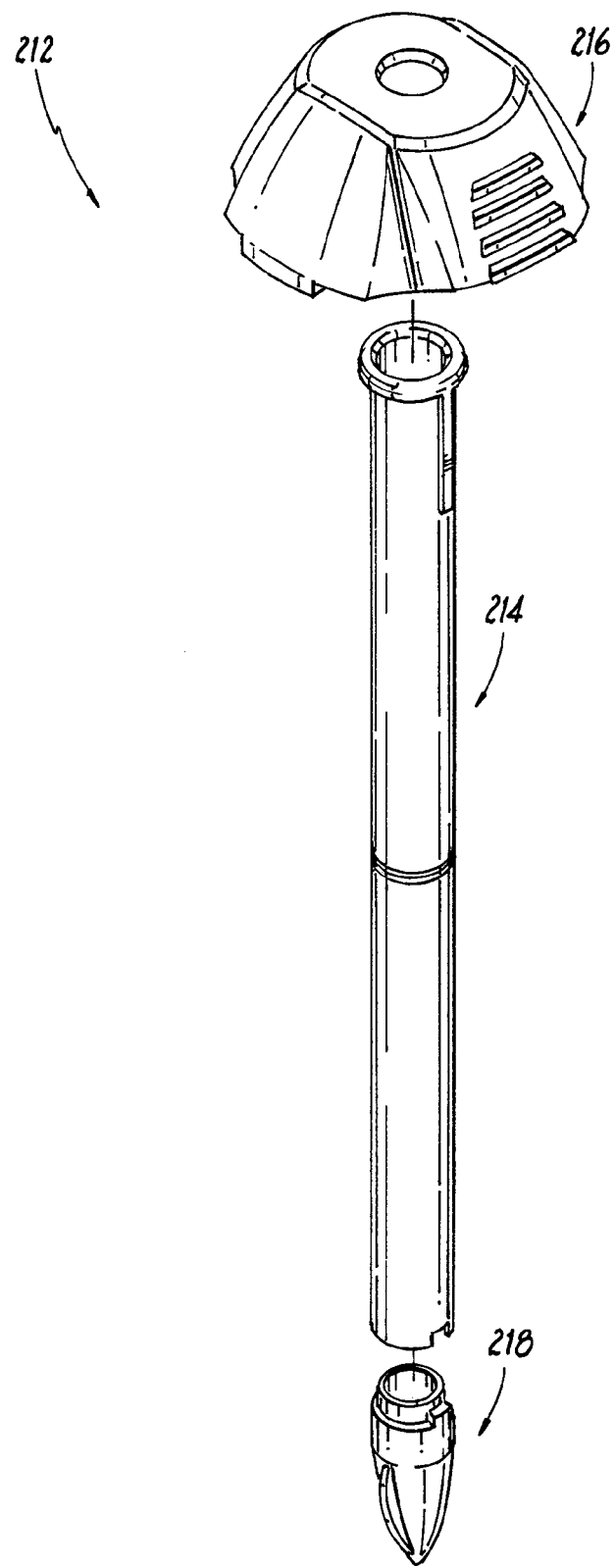
FIG. 10 is an exploded perspective view of another exemplary embodiment of an obturator constructed in accordance with this disclosure, showing a three piece obturator construction.
Figure 11:
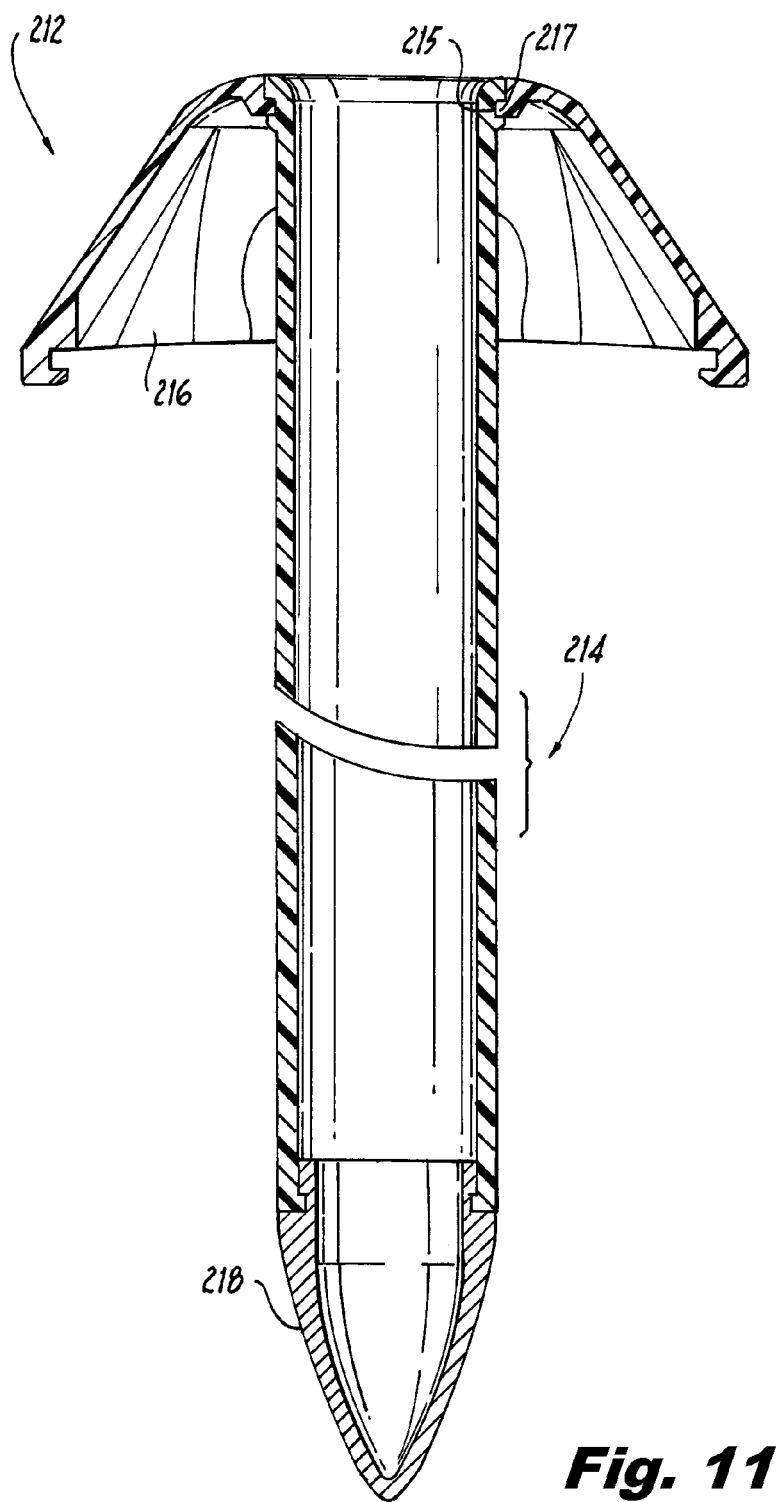
FIG. 11 is a cross-sectional side elevation view of the obturator of FIG. 10, showing the connection between the obturator body and the trocar cover.

In obturator 112, obturator body 114 is integral with trocar cover 116. It is also contemplated that these can be made as separate pieces joined together, as in obturator 212 in FIG. 10. Obturator 212 includes an obturator tip 218 that is attached to obturator body 214 in the same manner described above with respect to obturator tip 118. Trocar cover 216 is a separate piece that can be attached to obturator body 214 as shown in FIG. 11. Lip 217 of trocar cover 216 seats in detent 215 of obturator body 214. This allows trocar cover 216 and obtrurator body 214 to be made of two different materials. For example, trocar cover 216 can be made of a relatively flexible material to facilitate actuation of the latches as described above, and obturator body 214 can be made of a relatively rigid material to facilitate introduction to a surgical site.

Figure 12:
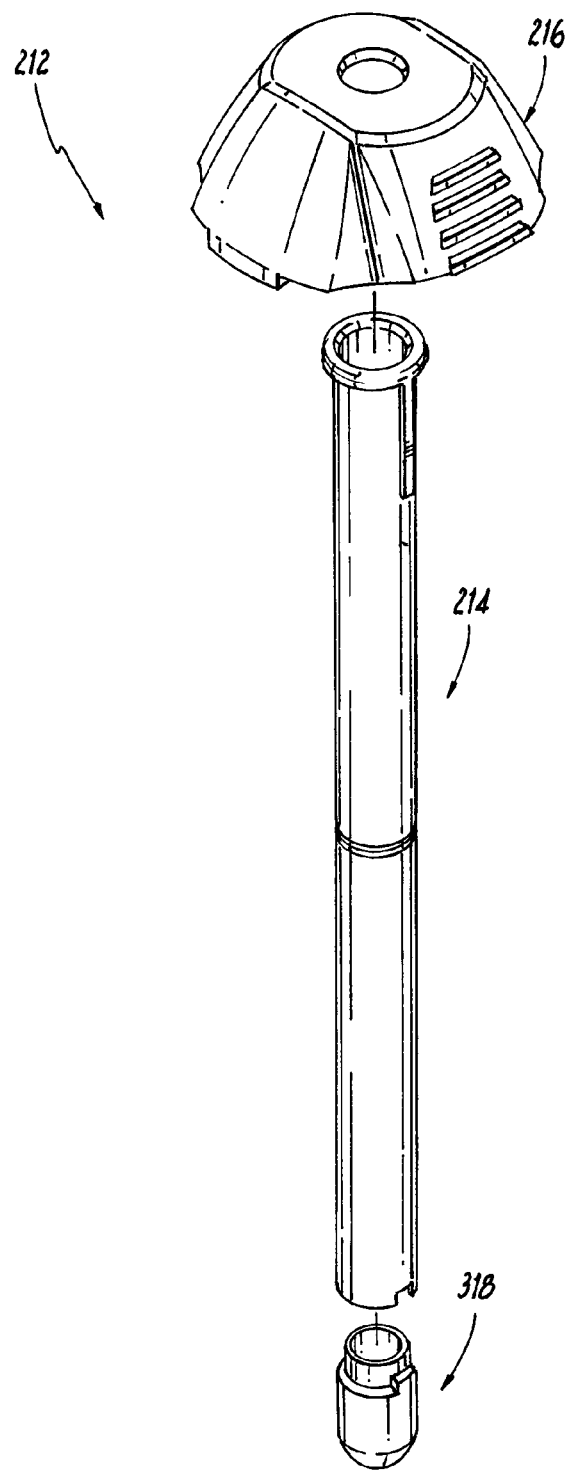
FIG. 12 is an exploded perspective view of the obturator of FIG. 10, showing another exemplary obturator tip in place of the one shown in FIG. 10.

With reference to FIG. 12, obturator 212 is shown with another exemplary embodiment of an obturator tip, namely obturator tip 318, which is generally blunt relative to obturator tips 118 and 218 described above. Those skilled in the art will readily appreciate that any other suitable tip geometry can be used as needed on an application by application basis without departing from the scope of this disclosure.

The methods and systems of the present disclosure, as described above and shown in the drawings, provide for trocars and obturators with superior properties including improved assembly and ease of use. While the apparatus and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A trocar assembly comprising:
a trocar including an elongated tubular member extending between a distal end configured to be inserted into a surgical site and a proximal end including a housing configured for introduction of surgical instruments into the tubular member, wherein the housing includes a pair of opposed latch receptacles; and
an obturator assembled into the tubular member of the trocar, wherein the obturator includes an elongated obturator body extending from a trocar cover to an opposed obturator tip, wherein the trocar cover includes a rim for engaging the housing of the trocar, wherein the trocar cover includes a pair of opposed latches extending radially inward from and extending distally from the rim, wherein the latches are releasably latched to the latch receptacles of the trocar, wherein the trocar cover includes a compliant mechanism operatively connected to release the latches from the latch receptacles, wherein the compliant mechanism includes a pair of opposed pinch regions circumferentially offset from the latches around the same rim, wherein the compliant mechanism is configured to move the latches from latched positions to release positions radially outward from the latched positions upon pinching the pinch regions toward one another.

2. A trocar assembly as recited in claim 1, wherein the trocar cover includes an anti-rotation key engaged to an anti-rotation key receptacle defined in the housing of the trocar to resist relative rotation of the trocar and obturator.

3. A trocar assembly as recited in claim 1, wherein each of the pinch regions includes a textured surface to facilitate actuation of the compliant mechanism.

4. A trocar assembly as recited in claim 1, wherein the obturator tip includes a latch receptacle and an anti-rotation key, wherein the obturator body includes a latch engaged in the latch receptacle of the obturator tip, and wherein the obturator body includes an anti-rotation key receptacle engaged to the anti-rotation key of the obturator tip.

5. A trocar assembly as recited in claim 4, wherein the obturator tip includes an engagement member extending into and engaged with an interior bore of the obturator body, wherein the engagement member includes a hard stop surface blocking a radially outward portion of the interior bore for providing a hard stop to endoscopes moving within the interior bore.

6. A trocar assembly as recited in claim 5, wherein the engagement member is sealingly engaged to the interior bore of the obturator body to prevent leakage between the obturator body and the obturator tip.

7. A trocar assembly as recited in claim 6, wherein the engagement member includes a full annular sealing surface sealed to the interior bore of the obturator body.

8. A trocar assembly as recited in claim 4, wherein the anti-rotation key is a first anti-rotation key, wherein the obturator tip includes a second anti-rotation key opposed to the first anti-rotation key, wherein the anti-rotation key receptacle is a first anti-rotation key receptacle, wherein the obturator body includes a second anti-rotation key receptacle opposed to the first anti-rotation key receptacle, wherein the first and second anti-rotation keys are engaged to the first and second anti-rotation key receptacles, respectively.

9. An obturator comprising:
an elongated obturator body extending from a trocar cover to an opposed obturator tip, wherein the trocar cover includes a rim for engaging a trocar, wherein the trocar cover includes a latch extending radially inward from and extending distally from the rim, wherein the trocar cover includes a compliant mechanism operatively connected to move the latch between a latched position and a release position radially outward from the latched position, wherein the compliant mechanism includes a pair of opposed pinch regions circumferentially offset from the latch around the same rim, wherein the compliant mechanism is configured to move the latch from the latched position to the release position radially outward from the latched position upon pinching the pinch regions toward one another.

10. An obturator as recited in claim 9, wherein the latch is a first latch, and wherein the trocar cover includes a second latch extending radially inward from the rim and opposed to the first latch.

11. An obturator as recited in claim 10, wherein each of the pinch regions includes a textured surface to facilitate actuation of the compliant mechanism.

12. An obturator as recited in claim 9, wherein the obturator tip includes a latch receptacle and an anti-rotation key, and wherein the obturator body includes a latch engaged in the latch receptacle, and wherein the obturator body includes an anti-rotation key receptacle engaged to the anti-rotation key.

13. An obturator comprising:
an elongated obturator body terminating distally in an obturator tip, wherein the obturator tip includes a latch receptacle and an anti-rotation key, wherein the obturator body includes a latch engaged in the latch receptacle, and wherein the obturator body includes an anti-rotation key receptacle engaged to the anti-rotation key, wherein the obturator tip includes an engagement member extending into and engaged with an interior bore of the obturator body, wherein the engagement member includes a full annular sealing surface proximal of the latch receptacle and anti-rotation key.

14. An obturator as recited in claim 13, wherein the engagement member includes a hard stop surface blocking a radially outward portion of the interior bore for providing a hard stop to endoscopes moving within the interior bore.

15. An obturator as recited in claim 14, wherein the engagement member is sealingly engaged to the interior bore of the obturator body to prevent leakage between the obturator body and the obturator tip.

16. An obturator as recited in claim 15, wherein the full annular sealing surface is sealed to the interior bore of the obturator body.

17. An obturator as recited in claim 13, wherein the latch receptacle is a first latch receptacle, wherein the obturator tip includes a second latch receptacle opposed to the first latch receptacle, wherein the latch is a first latch, wherein the obturator body includes a second latch opposed to the first latch, wherein the first and second latches are engaged to the first and second latch receptacles, respectively.

18. An obturator as recited in claim 13, wherein the anti-rotation key is a first anti-rotation key, wherein the obturator tip includes a second anti-rotation key opposed to the first anti-rotation key, wherein the anti-rotation key receptacle is a first anti-rotation key receptacle, wherein the obturator body includes a second anti-rotation key receptacle opposed to the first anti-rotation key receptacle, wherein the first and second anti-rotation keys are engaged to the first and second anti-rotation key receptacles, respectively.

* * * * *